(12) United States Patent
Zand

(10) Patent No.: US 9,937,081 B2
(45) Date of Patent: Apr. 10, 2018

(54) MOISTURE AND FEVER SENSING APPARATUS

(71) Applicant: Farnaz Zand, Burbank, CA (US)

(72) Inventor: Farnaz Zand, Burbank, CA (US)

(*) Notice: Subject to any disclaimer, the term of this patent is extended or adjusted under 35 U.S.C. 154(b) by 379 days.

(21) Appl. No.: 14/754,195

(22) Filed: Jun. 29, 2015

(65) Prior Publication Data

US 2016/0374867 A1    Dec. 29, 2016

(51) Int. Cl.
*G08B 21/00*  (2006.01)
*A61F 13/42*  (2006.01)

(52) U.S. Cl.
CPC ........ *A61F 13/42* (2013.01); *A61F 2013/421* (2013.01); *A61F 2013/426* (2013.01); *A61F 2013/429* (2013.01)

(58) Field of Classification Search
CPC ................ A61F 13/42; A61F 2013/421; A61F 2013/426; A61F 2013/429
USPC ...................................... 340/573.5
See application file for complete search history.

(56) References Cited

U.S. PATENT DOCUMENTS

| 5,197,958 A    | *  | 3/1993  | Howell    | A61F 13/42 604/361    |
| 2003/0020615 A1 | * | 1/2003  | Zand      | A61F 13/42 340/573.5  |
| 2004/0087922 A1 | * | 5/2004  | Bobadilla | A61F 13/42 604/361    |
| 2007/0270773 A1 | * | 11/2007 | Mackey    | A61F 13/42 604/361    |
| 2014/0324004 A1 | * | 10/2014 | Song      | A61L 15/56 604/359    |

* cited by examiner

*Primary Examiner* — Mark Rushing
(74) *Attorney, Agent, or Firm* — James E. Brunton

(57) ABSTRACT

A combined apparatus for indicating the elevated temperature of an infant and for sensing moisture in a diaper. The combined apparatus includes an elongated sensing strip made of highly efficient liquid absorption and transfer capillary wick material having a first end disposed in engagement with the diaper. The elongated sensing strip has a first side having a pair of screen-printed, spaced apart conductive ink bands which couple electrically at one end with a portable alarm unit and a second side having an elongated band of thermochromic ink printed thereon a segment of which is visible proximate the second end of the elongated sensing strip.

9 Claims, 7 Drawing Sheets

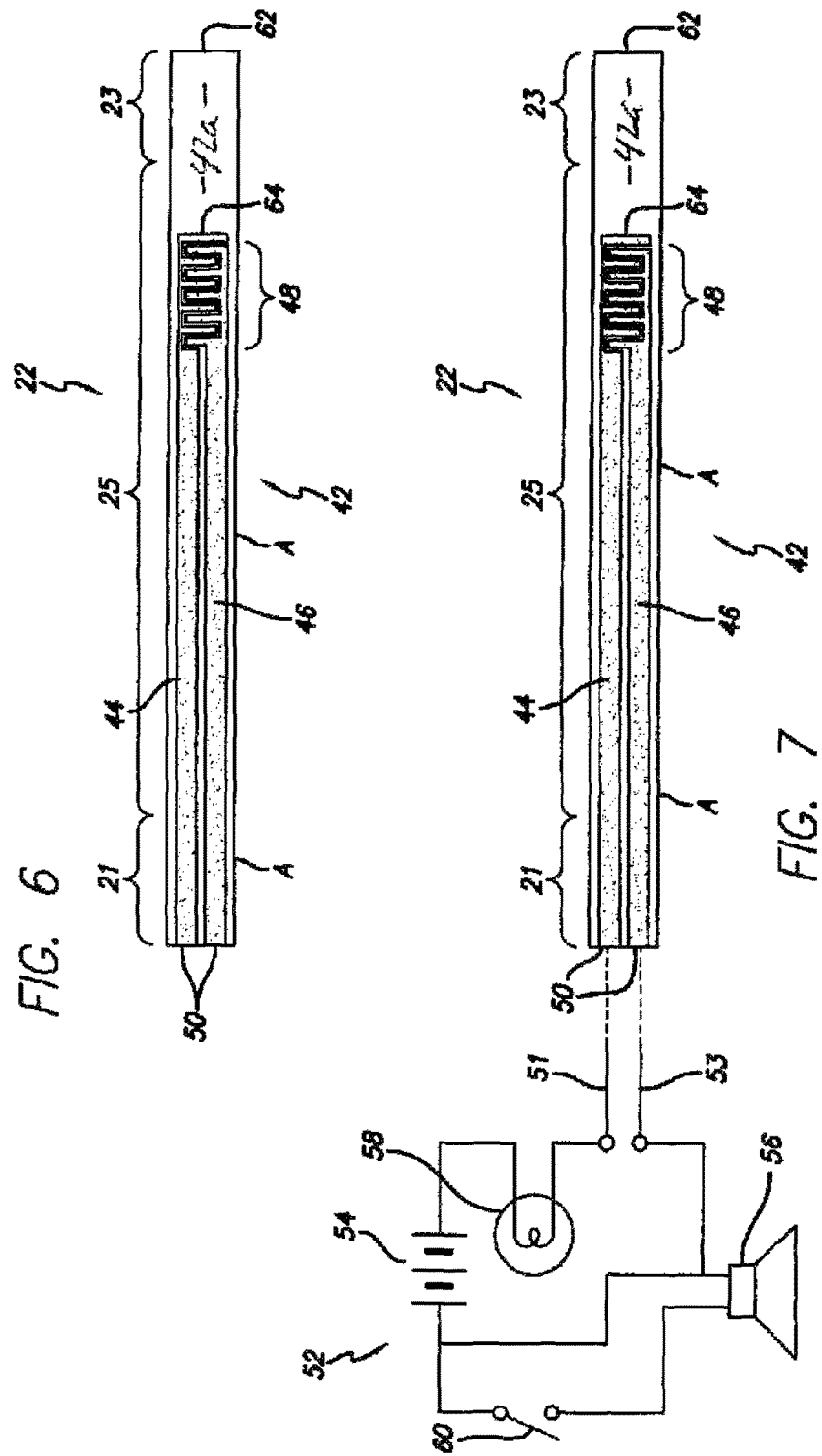

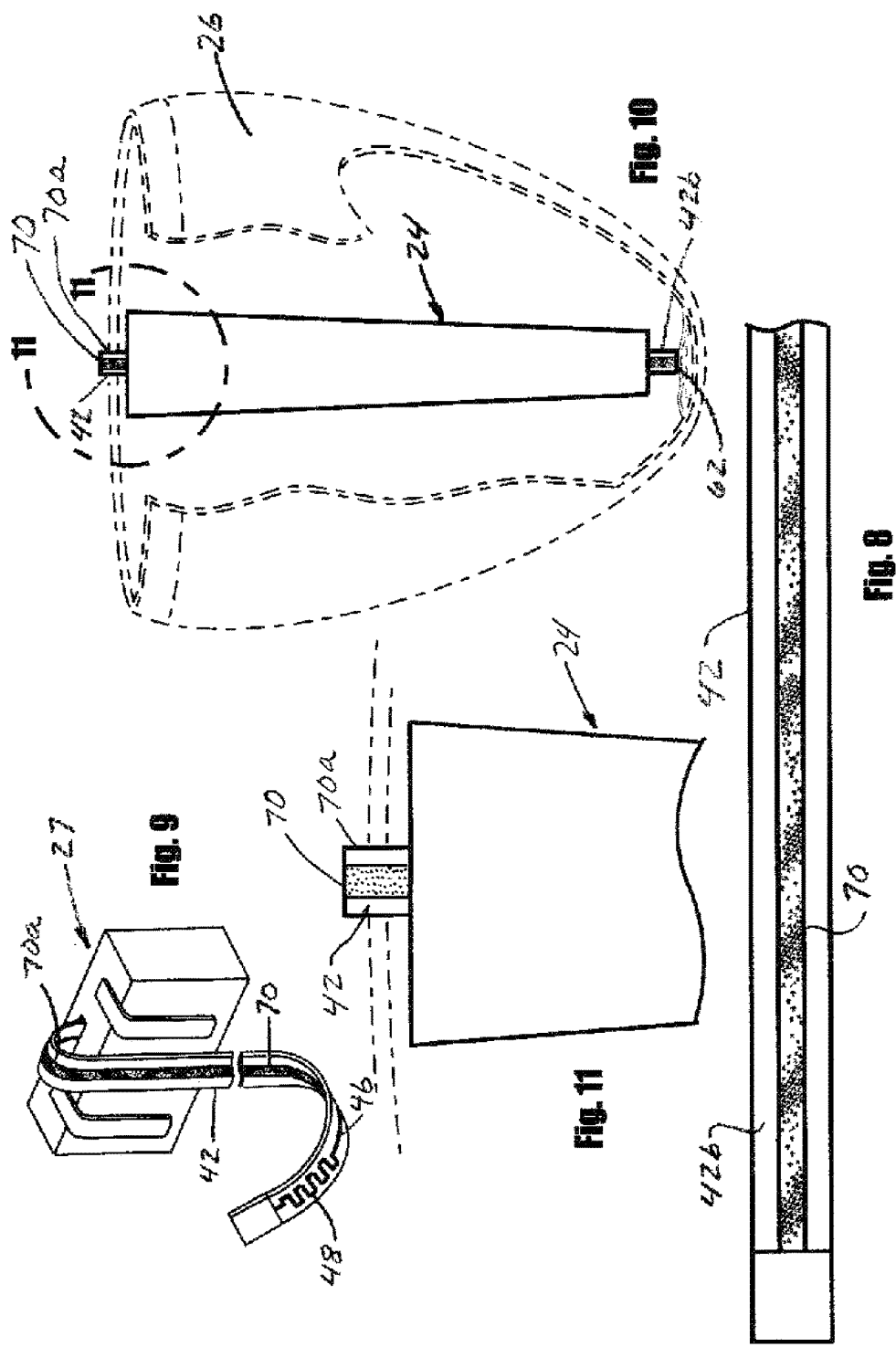

MOISTURE AND FEVER SENSING APPARATUS

CROSS-REFERENCE TO RELATED APPLICATIONS

Not applicable

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

Field of the Invention

The present invention relates generally to patient care devices and more particularly to a novel moisture sensing and elevated temperature indicating device. The combined apparatus of the invention continuously monitors the patient's temperature and senses urination in clothing articles such as diapers worn by young children and/or incontinent adults, respectively, and for emitting alarm signal(s) to alert a caregiver that a diaper change is needed.

Description of Related Art Including Information Disclosed Under 37 CFR 1.97 and 1.98

Bladder incontinence is a problem endemic in the very young and is cured only by intensive training as the young child goes through its second and third year of life requiring in the meantime, the constant use of diapers. The same problem can affect the elderly or the infirm or persons of any age who may have this problem because of physiological or psychological problems. A problem of this nature may be a major source of embarrassment. The mere fear of such incontinence can be a danger to the psychological welfare of persons already subject to severe psychological pressures due to other infirmities. Such people, both the very young and the infirm, often have no warning that their undergarments are being wet by urine until the undergarments are uncomfortably wet. There has always been a need for a device which can automatically warn either the person involved, or his/her caretaker (nurse or parent) that such undesirable leakage or wetness has occurred.

Various devices for detecting moisture or wetness such as caused by urination are known in the prior art. In diapers, the purpose of such devices is to set off an alarm when the diaper becomes wet. This permits a parent or other attendant to immediately tend to a newborn infant, toddler or an incontinent adult. Such devices usually include a pair of electrodes placed in the diaper which conduct electric current if wetness is detected. Prior art devices of this type, however, have numerous disadvantages such as requiring current-carrying conductors to pass mechanically through the diaper's plastic outer sheath, which may subject the skin of the child/incontinent adult to potentially high voltages, may be sensitive only in a limited area in the diaper, may accidentally respond to the wearer sitting on a wet or metal bench or park slide or may have other undesirable drawbacks.

The numerous disadvantages of the prior art urine sensing devices have been largely overcome by the highly novel and useful apparatus illustrated and described in U.S. Pat. No. 6,559,772 issued to the inventor named herein. As will become apparent from the discussion which follows, the novel and useful apparatus described in this patent has now been improved by the addition of novel means for continuously monitoring the temperature of the patient while at the same time standing ready to automatically alert a caregiver that a diaper change is needed.

Similarly, a wide variety of temperature sensing devices that operate on several different scientific principles have been suggested in the past. By way of example, one type of prior art thermometer uses thermochromic liquid crystals that are constructed in a planar shape and react to changes in temperature by changing color. This type of thermometer is discussed in U.S. Pat. No. 6,241,386 issued to Limburg et al. As discussed in this patent, thermochromic liquid crystals are typically made of twisted molecular structures comprising optically active mixtures of organic chemicals and include cholesteric compositions, chiral nematic formulations, and combinations of the two. Such crystals have been implemented in a variety of forms. One of the most prevalent examples is a temperature strip made by placing numerous thermochromic liquid crystal rectangles end to end. The rectangles are arranged so that, as the ambient temperature changes from lowest to highest readable temperature, the rectangles are individually illuminated sequentially from one end of the strip to the other.

Another prior art product that displays a change responsive to changes in temperature is discussed in U.S. Pat. No. 4,744,113 issued to Kogut. This product concerns a toilet training aid having a porous sheet of paper with an invisible picture thereon that is placed over a toilet bowl and produces an image when wetted by warm liquid.

In a similar vein, U.S. Pat. No. 4,725,462 issued to Kimura concerns the use of heat activated indicia on textiles. More particularly, Kimura uses thermochromatic colors formed into a textile to form an image. The indicia is not visible to the naked eye in the normal ambient temperatures but when subjected to a predetermined temperature, such as when immersed in bath water, an image appears to the user.

SUMMARY OF THE INVENTION

The present invention is directed to a combined apparatus for continuously monitoring the temperature of a patient and at the same time functioning to sense moisture at the patient's diaper. The combined apparatus includes an elongated sensing strip made of highly efficient liquid absorption and transfer capillary wick material having a first end disposed in engagement with the diaper. The elongated sensing strip has a first side having a pair of screen-printed spaced apart conductive ink bands which couple electrically at one end with a portable alarm unit and a second side having an elongated band of thermochromic ink printed thereon a segment of which is visible proximate the second end of the elongated sensing strip.

In accordance with one aspect of the present invention, the sensing strip is made of a highly efficient capillary liquid transfer wick material.

In accordance with another aspect of the present invention, the sensing strip comprises a substantially short first portion disposed at the first location, a substantially long second portion disposed adjacent the substantially short first portion and a third portion disposed adjacent the second portion.

In accordance with still another aspect of the present invention, the sensing means includes at least two spaced apart conductive ink bands screen-printed on a first side of the second and third portions of the wick strip, a waterproof pouch for enclosing the second portion, and an alarm signaling circuit operatively coupled to the conductive ink bands on the third portion. The waterproof pouch comprises an opening at a first end and a pocket at a second end for removably receiving a portable alarm unit containing the alarm signaling circuit, the substantially short first portion of the wick strip protruding from the first end.

In accordance with yet another extremely important aspect of the present invention, the sensing apparatus of the present invention further includes an elongated band of thermochromic ink that is printed on the opposite side of the wick strip from the site upon which the conductive ink bands are printed. During use, a portion of this band is clearly visible to the caregiver proximate the second end of the elongated sensing strip.

These and other aspects of the present invention will become apparent from a review of the accompanying drawings and the following detailed description of the preferred embodiments of the present invention.

BRIEF DESCRIPTION OF THE DRAWINGS

FIG. 6 is a top view of a sensing strip in accordance with the present invention;

FIG. 7 is a schematic view of the moisture sensor of FIG. 6 shown coupled to an electrical circuit in accordance with the present invention;

FIG. 8 is a bottom view of a sensing strip in accordance present invention;

FIG. 9 is a generally perspective, diagrammatic view of the sensing strip and the alarm signal unit of the present invention.

FIG. 10 is a fragmentary view similar to FIG. 3 looking into the undergarment at the body side of the pouch-like diaper insert and sensing strip of the invention;

FIG. 11 is a greatly enlarged view of the area identified as 11-11 in FIG. 10.

DESCRIPTION OF THE PREFERRED EMBODIMENT

Figure 2:
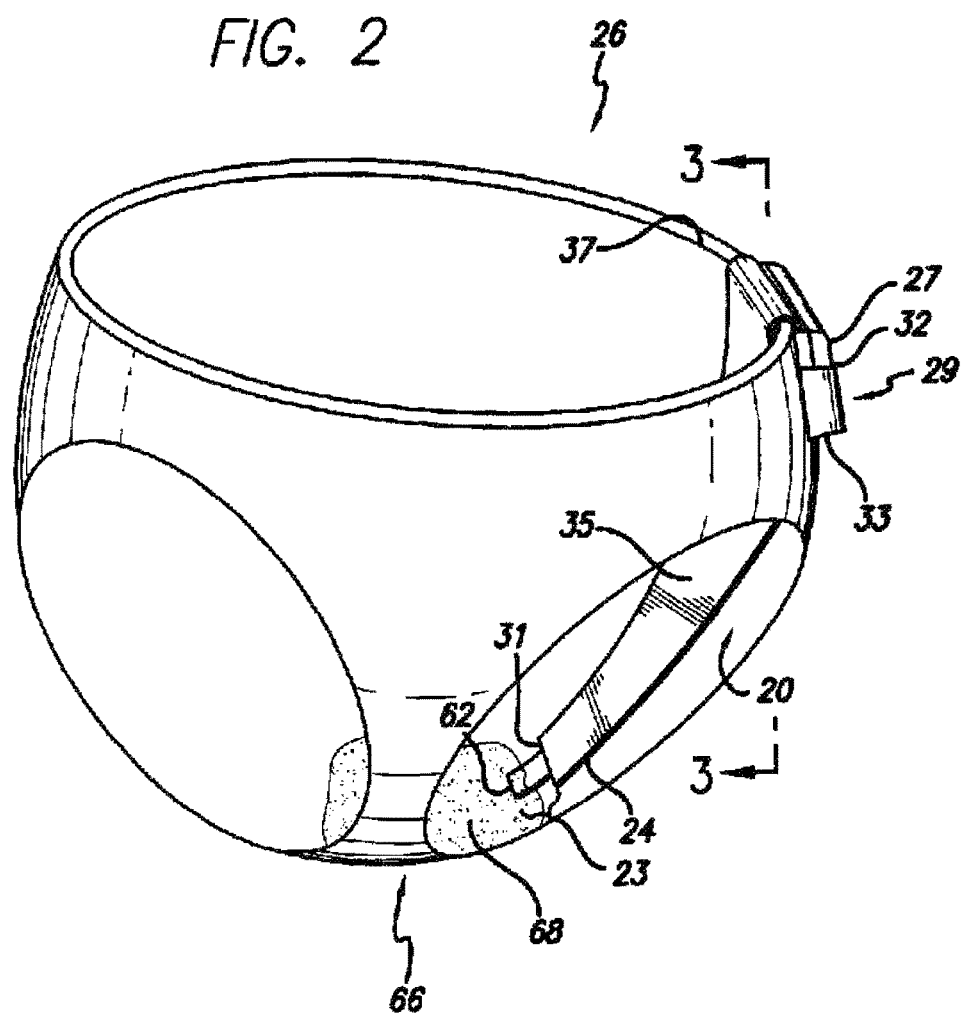
FIG. 2 is a perspective view of an undergarment (such as a diaper) with the temperature indicating and moisture sensing apparatus of FIG. 1 applied to the undergarment in accordance with the present invention.
Figure 3:
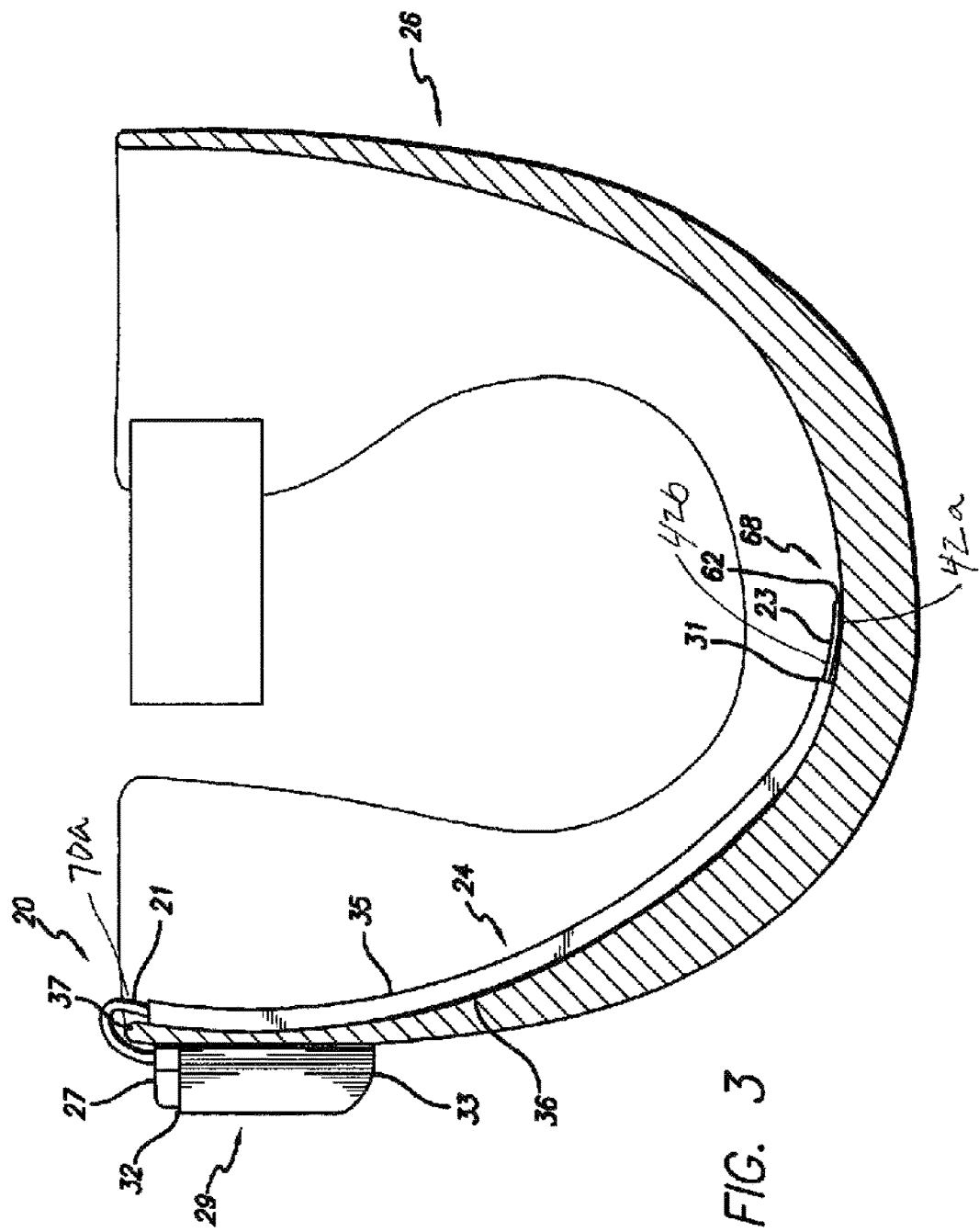
FIG. 3 is a cross-sectional view taken along section line 3-3 of FIG. 2.
Figure 5:
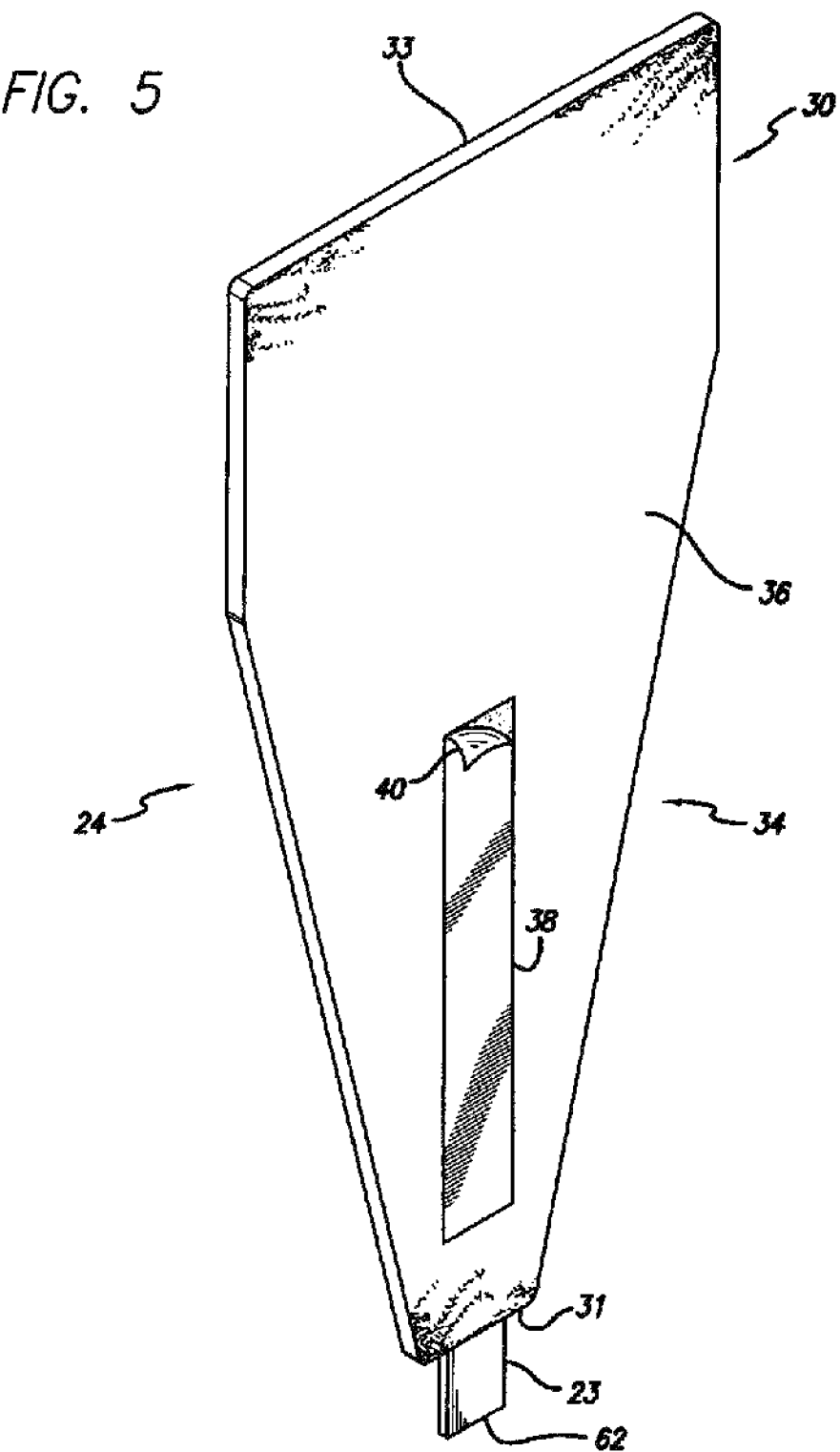
FIG. 5 is a back perspective view of a diaper insert partially enclosing a sensing strip in accordance with the present invention.

The present invention is directed to a combination elevated temperature sensing and moisture sensing apparatus generally designated in the drawings by the numeral 20. The apparatus continuously monitors temperature of the user and functions to detect urine in clothing articles such as diapers for young children and/or incontinent adults and here comprises a disposable pouch-like diaper insert 24 partially enclosing a disposable sensor 22. Diaper insert 24 is preferably designed to be waterproof on the inside, i.e. around the enclosed portion of sensor 22, and is adapted on one side to be adhesively affixed to the inside of a young child's or an incontinent adult's diaper 26 (FIGS. 2, 3 and 5).

Figure 1:
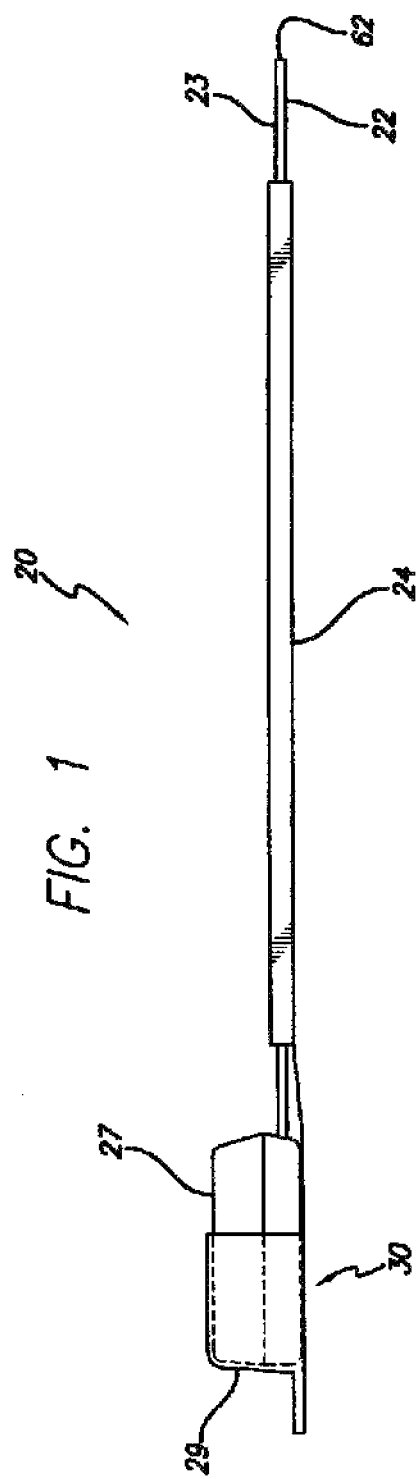
FIG. 1 is a side elevational view of a combined temperature indicating and moisture sensing apparatus in accordance with the present invention.

Disposable sensor 22 (FIGS. 6 and 7) is preferably constructed from an elongated, generally rectangular strip of a highly efficient capillary liquid transfer wick material 42 designed to enhance absorption, retention and transfer of liquid by capillary attraction. A wick 42 having a length of about 7.75 inch, a width of about 0.5 inch and a thickness of about 0.063 inch may be used to practice the invention. A wick of this type may be purchased, for example, from Filtrona Richmond, Inc. of Richmond, Va. under the trademark name TRANSPAD® Wick strip 42 has a first, or outer side 42a and a second, or inner side 42b (FIGS. 6 and 8) and here comprises a substantially short first portion 23 which protrudes out of a first open end 31 (FIGS. 4 and 5) of diaper insert 24 and is intended for placement in the crotch area of a young child's or incontinent adult's diaper 26 (FIGS. 2 and 3) to allow rapid transfer of moisture (such as from urination) by capillary attraction to an adjacent substantially long second portion 25 (FIG. 6). In one example, first portion 23 may be approximately 0.75 inch long. Second portion 25 is preferably fully enclosed by the waterproof inner walls of diaper insert 24 to prevent loss of transferred urination to the diaper padding. Second portion 25 is also adapted on first side 42a (FIGS. 6 and 7) to conduct current in the presence of transferred moisture (urination) from the crotch area of the diaper. Wick strip 42 further comprises a third portion 21 (FIG. 6) disposed adjacent to second portion 25. Third portion 21 protrudes out of diaper insert 24 (FIG. 4) to allow for electrical coupling at an end 50 to an electrical circuit 52 (FIG. 6) which is part of a relatively compact portable and preferably re-usable alarm signal unit 27 (FIG. 1).

Alarm signal unit 27 contains a custom-made electronic circuit board (not shown) adapted to provide light and/or sound and/or vibratory alarm signals or the like to alert a caregiver that a young child or incontinent adult is in need of a diaper change. Alarm signal unit 27 may be adapted to send a radio signal to a receiver on a remote caregiver and is preferably removably coupled to diaper insert 24 by manually inserting alarm signal unit 27 in a pocket 29 formed in a tail portion 30 of diaper insert 24 (FIG. 1). In one example, portable alarm signal unit 27 may have the following approximate exterior dimensions: 1.5 inch length by 1.4 inch width by 0.2 inch thickness and may be powered by a small 3-volt battery (not shown).

Second side 42b of the wick strip 42 is preferably adhesively attached to the waterproof inner wall of diaper insert 24. Other means of securing wick 42 inside diaper insert 24 may be used, provided such other securing means agree with the intended purpose of the present invention.

Figure 4:
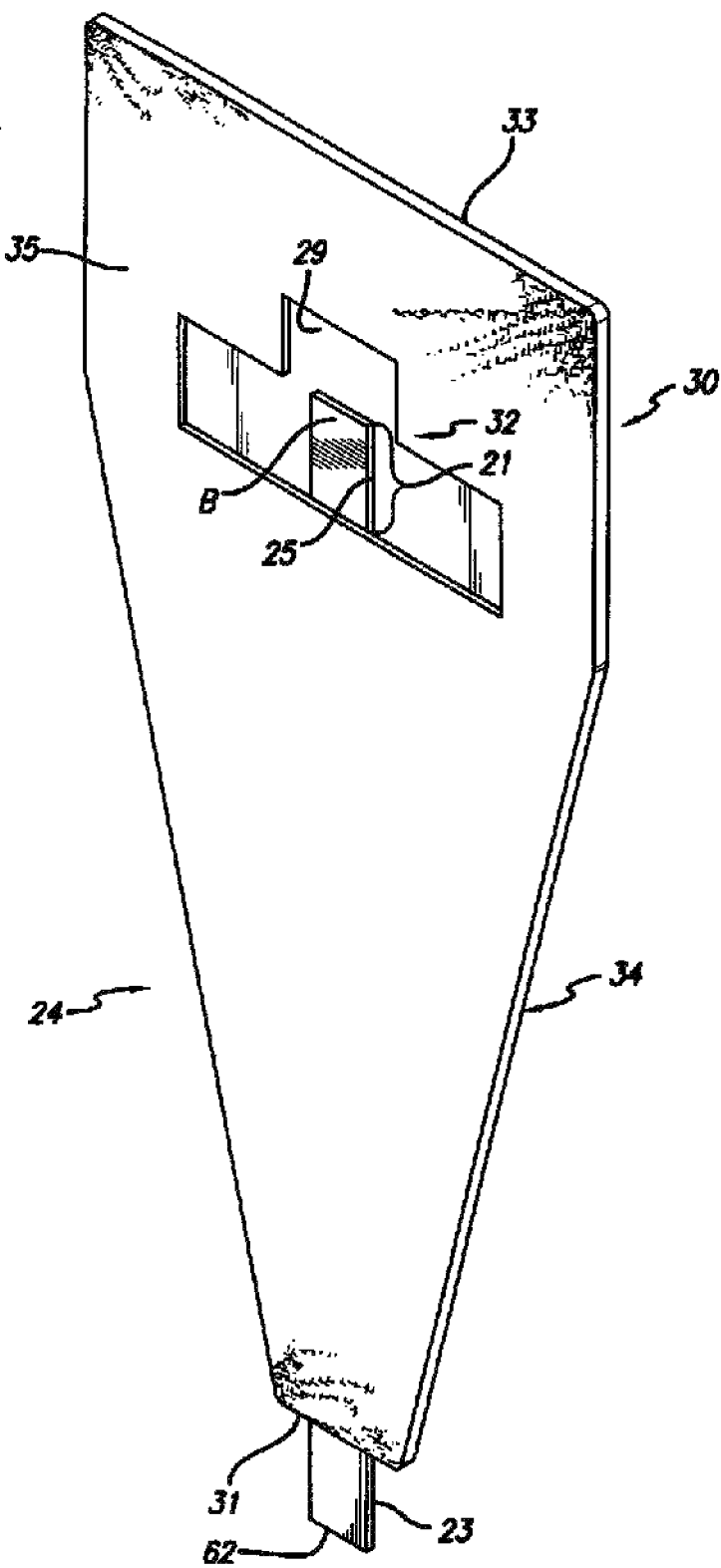
FIG. 4 is a front perspective view of a diaper insert partially enclosing a sensing strip in accordance with the present invention.

Diaper insert 24 is preferably made from at least one layer of thin flexible material reinforced with a waterproof plastic backing layer on one side which, in one embodiment of the present invention, is cut, folded substantially in the middle such that the waterproof plastic backing remains on the inside to form the inner wall and then heat-sealed at the open edges on each of two opposing sides to form a relatively flat elongated pouch or envelope which is open at first end 31 (FIGS. 4 and 5). Pouch-like diaper insert 24 may be constructed from dental bib-type paper which is usually reinforced on one side with a thin plastic waterproof backing material. Dental-bib type paper may be purchased from medical/dental suppliers such as Henry Schein, Inc. of Melville, N.Y.

As generally illustrated in FIGS. 4-5, tail portion 30 of pouch-like diaper insert 24 is generally rectangular-shaped, closed at a second end 33 (since end 33 represents the line of folding the dental bib material to form diaper insert 24) and provided on a side 35 with a polygonal cutout 32 to allow third portion 21 of wick strip 42 to electrically couple with electrical circuit 52 (FIG. 7) of alarm signal unit 27. Cutout 32 also serves as the opening for pocket 29 (FIG. 1) of tail portion 30 of diaper insert 24. Tail portion 30 preferably folds over a diaper waistline 37 (FIGS. 2 and 3) to form pocket 29 on the outside of diaper 26 for inserting alarm signal unit 27.

A remaining portion 34 of diaper insert 24 is generally trapezoidal-shaped, open at first end 31 (FIGS. 4 and 5) to accommodate outwardly protruding substantially short first portion 23 of wick strip 42 and preferably provided at an opposite side 36 (FIG. 5) with a double-sided adhesive strip 38 which has a peelable backing 40 (FIG. 5). Backing 40 is peeled off by the caregiver to adhesively attach side 36 of diaper insert 24 to the inside of diaper 26 (FIGS. 2 and 3) such that first portion 23 of wick strip 42 is preferably disposed in the diaper crotch area (FIGS. 2 and 3) before the diaper can be used by a young child or an incontinent adult. Other means attaching diaper insert 24 to the inside of diaper 26 may be used such as sewing, laminating in place or the like, provided such other attachment means fall within the scope of the present invention.

In accordance with the preferred embodiment of the present invention, side 42a of second and third portions of wick strip 42 is adapted to conduct electric current by screen-printing on it a pair of elongated, spaced apart and generally parallel conductive ink bands 44, 46 as generally depicted in FIGS. 6 and 7. Conductive ink bands 44, 46 are substantially identical, i.e. of the same width, length and overall configuration. The preferred spacing between conductive ink bands 44, 46 is about one half the width of a conductive ink band (44 or 46). Conductive ink is formed by mixing carbon powder or silver powder with acrylic resin and solvent and then dispersing the same. Conductive ink may be applied to a variety of substrates by screen printing, dipping and syringe dispensing. Conductive ink suitable for practicing the invention may be purchased, for example, from Creative Materials Incorporated of Tyngsboro, Mass. The preferred thickness of each conductive band (44, 46) is about 0.002 inch-0.003 inch. Conductive ink bands 44, 46 terminate at one end with a tortuous conductive ink pattern 48, one example of which is shown in FIGS. 6 and 7, designed to increase the moisture contact surface area. Tortuous conductive ink pattern 48 has a front end 64 (FIGS. 6 and 7) preferably disposed in close proximity to substantially short first portion 23. In one example, the distance moisture (urination) has to travel by capillary attraction between front end 64 and first portion 23 may be 0.75 inch. At the opposite end, conductive ink bands 44, 46 extend all the way to end 50 of third portion 21 of wick strip 42 (FIGS. 6 and 7) to couple electrically to leads 51, 53 of electrical circuit 52 (FIG. 7). A person skilled in the art would readily recognize that various other conductive ink patterns may be implemented in lieu of tortuous conductive ink pattern 48 to increase moisture contact surface area in close proximity to substantially short first portion 23 (which is placed in the crotch area of diaper 26), provided such other patterns fall within the scope of the present invention.

Electrical circuit 52 (FIG. 7) is shown as a simplified circuit including a power source or battery 54, an audio alarm device 56, a visual alarm (e.g., colored lights) device 58 and a manual switch 60. Circuit 52 may be disposed in a light-weight plastic housing (not shown) to form a portable alarm signal unit. A person skilled in the art would appreciate that other types of alarm devices may be connected to simplified circuit 52, e.g. a vibratory alarm device or the like.

Simplified circuit 52 is merely one example of an electrical circuit which may be used to practice the present invention. Other more complex circuits may be utilized depending on the needs of the caregiver providing such circuits do not deviate from the intended purpose of the present invention.

In accordance with the general principles of the present invention and assuming manual switch 60 in simplified electrical circuit 52 (FIG. 7) is closed, any amount of moisture (from urination) 68 (FIG. 2) in crotch area 66 of diaper 26 coming in contact with a tip 62 (FIG. 2) of first portion 23 of wick strip 42 is being quickly transferred up (via the highly efficient wick strip material 42) to tortuous conductive ink pattern 48 of second portion 25 by capillary attraction. Transferred moisture (from crotch area 66) coming in contact with tortuous conductive ink pattern 48 will short circuit the conductive ink bands 44, 46 (i.e. close circuit 52) triggering alarm devices 56, 58 so as to alert the caregiver that a diaper change is required. A person skilled in the art would readily appreciate that the distance moisture 68 travels to reach tortuous conductive ink pattern 48, which in the above example is about 1.5 inch, is substantially shorter than the distance moisture has to travel in the above-described prior art moisture detecting device which used a capillary strip placed in the diaper crotch area and integrated electrical wires (electrodes) disposed far away at the waistline of the diaper. In one example and in accordance with the general principles of the present invention, typical potential and current conducted between conductive ink bands 44, 46 may be about 3 volts and a few microamperes, respectively, i.e. novel moisture sensing apparatus 20 eliminates all of the above-mentioned prior art health safety concerns.

Screen-printing two spaced apart conductive ink bands directly on wick strip 42 instead of attaching or incorporating two plain electrical wires on wick strip 42 reduces the overall cost of the moisture sensing apparatus and provides additional advantages such as using lower potentials, conducting very low currents and the like. The screen-printed conductive ink bands are flexible electrical conductors with a larger overall surface current area than plain electrical wires and are also less likely to be damaged during use alleviating any potential safety concerns a caregiver or user may have.

An extremely important feature of the improved apparatus of the present invention resides in the provision on the second side 42b of wick strip 42 of a temperature sensor comprising a thermochromatic material chosen from a group comprising leuco dyes. In one form of the invention, the thermochromatic material comprises a strip 70 of thermochromatic ink that is applied to the second side 40b of the wick along its entire length (see FIG. 8). Strip 70 preferably has a width of between 2 and 4 mm. As best seen by referring to FIGS. 3, 10 and 11 of the drawings, with this construction the portion 70a of strip 70 that is located proximate the interconnection of the wick 42 with the signal unit 27 is exposed so that the color change of the strip indicating an elevated temperature will be clearly visible to the caregiver.

The thermochromatic ink used to form strip 70 comprises temperature-sensitive dyes (or inks) called leucodyes. Leucodyes are organic (carbon-based) chemicals that change color when heat energy makes their molecules shift back and forth between two subtly differently structures known as the leuco (colorless) and non-leuco (colored) forms which start off transparent (or have a particular color) and become visible (or change to a different color) as the temperature rises. Organic leuco dyes are available for temperature ranges between about −5° C. (23° F.) and 60° C. (140° F.), in wide range of colors. The color change usually happens in a 3° C. (5.4° F.) interval. While thermochromatic inks are available from numerous sources, a thermochromatic ink offered for sale by LCR Hallcrest LLC of Glenveiw, Ill. is suitable for forming strip 70.

In using the apparatus of the present invention in the manner illustrated in FIGS. 3 and 10 of the drawings, the thermochromatic strip 70 will function to continuously monitor the temperature of the wearer of the diaper. In the event that the body temperature of the wearer exceeds normal body temperature of approximately 37° C., the strip will dramatically change color to immediately signal to the caregiver the existence of a higher than normal body temperature and fever.

While the present invention has been described in detail with regards to the preferred embodiments, it should be appreciated that various modifications and variations may be made in the present invention without departing from the scope or spirit of the invention. In this regard it is important to note that practicing the invention is not limited to the applications described hereinabove. Many other applications and/or alterations may be utilized provided such other applications and/or alterations do not depart from the intended purpose of the present invention.

I claim:

1. A combined moisture sensing and temperature sensing apparatus connected to a wearer and comprising:
    (a) a strip of highly efficient capillary liquid transfer wick material having first and second sides and first and second ends, said first side having a first portion at said first end of said strip, a second portion disposed adjacent said first portion and a third portion disposed at said second end adjacent said second portion, said wick material being adapted to efficiently absorb and transfer moisture via capillary attraction from said first end to said second end;
    (b) at least two spaced apart electrically conductive ink bands disposed on said first side of said strip of wick material proximate to said second and third portions;
    (c) an elongated band of thermochromic ink disposed on said second side of said strip of wick material, said elongated band of thermochromatic ink functioning to dramatically change color in the event that the temperature of the wearer exceeds approximately 37 degrees centigrade; and
    (d) a waterproof pouch for enclosing said second portion of said strip of wick material.

2. The apparatus as defined in claim 1 in which said thermochromic ink comprises leucodyes.

3. The apparatus as defined in claim 1 in which said elongated band of thermal chromatic ink has a width of between approximately 2 mm and 4 mm.

4. The apparatus as defined in claim 1, wherein said waterproof pouch comprises an opening at a first end and a pocket at a second end for removably receiving a portable alarm unit containing an alarm signaling circuit, said first portion of said wick strip protruding from said first end of said pouch.

5. A combined moisture sensing and temperature sensing apparatus connected with a patient and comprising:
    (a) a strip of highly efficient capillary liquid transfer wick material having first and second sides and first and second ends, said strip having a first portion at said first end, a second portion disposed adjacent said first portion and a third portion disposed at said second end adjacent said second portion, said strip being adapted to efficiently absorb and transfer moisture via capillary attraction from said first end to said second end;
    (b) at least two spaced apart electrically conductive ink bands disposed on said first side of said strip of wick material;
    (c) an elongated band of thermochromic ink disposed on said second side of said strip of wick material, said thermochromic ink comprising leucodyes and extending between said first and second ends of said capillary liquid transfer wick material, said elongated band of thermochromatic ink functioning to dramatically change color only in response to the patient's temperature exceeding about 37 degrees centigrade; and
    (d) a waterproof pouch for enclosing said second portion of said strip of wick material.

6. The apparatus as defined in claim 5 in which said elongated band of thermal chromatic ink has a width of between approximately 2 mm and 4 mm.

7. The apparatus as defined in claim 5, wherein said waterproof pouch comprises an opening at a first end and a pocket at a second end for removably receiving a portable alarm unit containing an alarm signaling circuit, said first portion of said wick strip protruding from said first end of said pouch.

8. A sensing apparatus connected to a user and comprising a strip of capillary liquid transfer wick material having first and second sides, said sensing apparatus being monitored by a caregiver and including:
    (a) a moisture sensing assembly connected to said first side of said strip of wick material for providing an audio signal to the caregiver in response to exposure of said strip of wick material to moisture, said moisture sensing assembly comprising:
        (i) at least two spaced apart electrically conductive ink bands disposed on said first side of said strip of wick material; and
        (ii) an alarm signal unit connected to said electrically conductive ink bands; and
    (b) an elevated temperature sensing assembly disposed on said second side of said strip of wick material for providing a visual signal to the caregiver in response to exposure of said strip of wick material to a temperature greater than about 37° C., said elevated temperature sensing assembly comprising a band of thermochromatic ink disposed on said second side of said strip of wick material.

9. The apparatus as defined in claim 8, wherein said thermochromic comprising leucodyes and wherein said visual signal to the caregiver comprises a dramatic change in the color of said thermochromatic ink.

* * * * *